Figure 1:
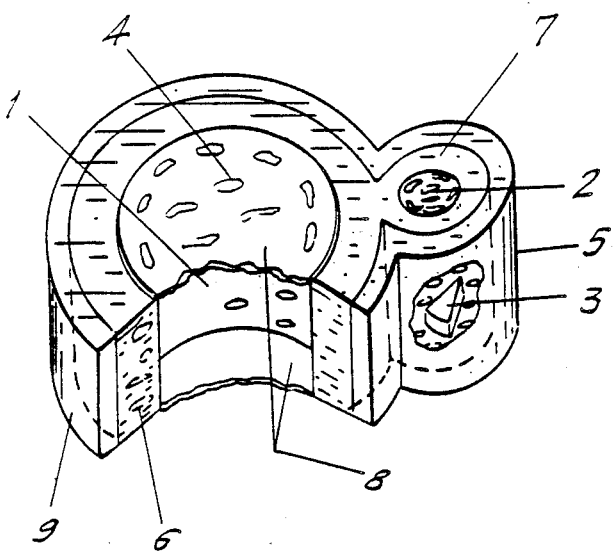

United States Patent [19]

Wang

[11] Patent Number: 4,976,695
[45] Date of Patent: Dec. 11, 1990

[54] IMPLANT FOR PERCUTANEOUS SAMPLING OF SEROUS FLUID AND FOR DELIVERING DRUG UPON EXTERNAL COMPRESSION

[76] Inventor: Paul Y. Wang, 47 Marblemount Crescent, Agincourt, Ontario, Canada, M1T 2H5

[21] Appl. No.: 213,092

[22] Filed: Jun. 29, 1988

[30] Foreign Application Priority Data

Apr. 7, 1988 [CA] Canada ................................. 563476

[51] Int. Cl.$^5$ ............................................ A61M 37/00
[52] U.S. Cl. ...................... 604/132; 604/93; 128/760
[58] Field of Search ............... 418/153; 604/132, 133, 604/896, 891.1, 93, 175, 181, 183

[56] References Cited

U.S. PATENT DOCUMENTS 4,209,014  6/1980  Sefton .................................. 604/132

Primary Examiner—Randall L. Green
Assistant Examiner—Randy Shay
Attorney, Agent, or Firm—Ostrolenk, Faber, Gerb & Soffen

[57] ABSTRACT

An implant comprises interconnected compartments with intlet and outlet and can be used for sampling of entered serous fluid or to hold drug concentrate for selective delivery, if desired. The compartments are formed by sealing around porous foam rings between a top and a bottom layer of biocompatible elastic membrane with a polymer paste which sets to form a rubbery shell. The top membrane layer over the compartment is punctured to create a small resealable channel. Upon subcutaneous implantation, serous fluid under hydrostatic pressure seeps into the interior through the puncture orifice. The entered fluid may be withdrawn by an hypodermic syringe through the rubbery side wall to obtain serum-borne bioactive materials. If a drug concentrate is included, the entered fluid will dissolve some of the drug therein. When delivery is required, external sidewise compression of the elastic compartment over the skin fold expels the drug containing solution therein through the orifice.

11 Claims, 1 Drawing Sheet

4,976,695

IMPLANT FOR PERCUTANEOUS SAMPLING OF SEROUS FLUID AND FOR DELIVERING DRUG UPON EXTERNAL COMPRESSION

FIELD OF THE INVENTION

This invention relates to a small implantable device which can be used to sample serous fluid containing bioactive materials which seeps into the interior through a resealable orifice thereon. If required, a drug concentrate can be included therein, and a desired dose dissolved in the entered fluid can be dispensed through the orifice by brief external compression of the implant over the skin fold.

BACKGROUND OF THE INVENTION

Collections of serous fluid containing bioactive substances, such as interferon, antibodies, hormones, etc., are conventionally carried out first by venopuncture with a large size needle to draw the fresh whole blood. The procedure involves discomfort to the subject, and risk of introducing infective organisms into the blood stream which circulates the whole body. Further, the cellular and coagulative components of the blood sample obtained must be separated to yield the serum part which theoretically amounts to about 50% of the original blood volume. However, in practice, the yield is often less due to entrapment in the gel formed by the blood clot. Therefore, an implant which allows the penetration of serous fluid for collection, when required, will be very desirable.

An implant is also needed to deliver medicament that may be required on a sustained or intermittent basis. These implantable drug delivery devices come in many forms, designs, sizes and principles of operation. Generally, they can be classified into 2 categories. The physical pumps deliver a drug solution by electrically propelled roller pumps or by a collapsible bellow compressed under the pressure of a volatile liquid. These pumps are bulky, and have a maximum drug reservoir capacity of about 45 ml which must be refilled frequently. In addition, only drugs that are soluble and stable in solution can be infused. In the other category are the smaller diffusional implants which mainly operate on 2 design variations. The first one is to disperse a small amount of the active agent in a solid excipient mass which is either inert or hydrolyzable by body fluid to facilitate the outward diffusion, especially of drugs with molecular weight >1,000 daltons. The other design is to put a drug solution in a flexible compartment with an exit orifice. A part of this compartment is surrounded by an osmotic agent which is enclosed further by a rigid, but permeable capsule. The body fluid imbibed into the capsule due to the osmotic agent compresses the drug compartment and expels the drug solution through the orifice. However, these diffusional implants are not readily amenable to the periodic augmentation in drug doses often required, e.g., in the treatment of diabetes by insulin, or to interruption of medicament, e.g., in contraception which requires steroid hormone daily for 21 days in a month.

In consideration of the aforementioned, a novel implantable device should be small for easy insertion, and should allow the penetration of serous fluid for sampling and harvesting of bioactive materials, or dissolution of a drug, if included therein, for dispensing on demand. If required, replenishment of the medicament should be readily implemented to last for a reasonable period of time. Further, when used as a drug delivery device, it should be able to discharge a drug in small amount, but if required, an increase in dose can also be implemented.

SUMMARY OF THE INVENTION

It is an objective of the present invention to provide an implantable reservoir device which collects serous fluid containing bioactive substance for percutaneous sampling. It is another objective of the present invention to provide an implantable drug delivery device which is small enough for subcutaneous insertion without requiring a large skin incision, while being capable of containing enough drug to last for several weeks.

It is still another objective of the present invention to provide a biocompatible device which is implantable and will deliver a drug by non-invasive external compression.

It is a further objective of the present invention to provide an implantable drug delivery device which can be refilled percutaneously if required.

The present invention provides a small device fabricated by attaching several porous foam rings of suitable annular width to form delivery and reservoir compartments. The porous foam serves as a lining to entrap solid drug particles and acts as a depot, if required, or filter between the interconnecting compartments. The interconnected foam rings are sealed around and between a top and a bottom layer of polymer membrane by a room temperature setting silicone rubber or similar elastomeric material. Finally, the top membrane of the delivery compartment is pierced with a sizeable needle to create a resealable orifice.

DESCRIPTION OF THE INVENTION

For use as a reservoir to collect serous fluid containing bioactive substances, the device as shown in FIG. 1, with just a single reservoir compartment 1 or with the additional interconnected compartment serving as reservoir 2 as well, is implanted subcutaneously, for example, into an animal which has been previously immunized with an antigen to produce specific antibodies. Within a few days after implantation, serous fluid seeps into the interior of the device. The fluid collected therein can be withdrawn percutaneously through a small gauge hypodermic needle from the implanted device for test of the specific antibodies or other bioactive materials present therein. The fluid can be withdrawn frequently and used at once without further processing. In comparison, the current practice is to collect the whole blood from an accessible vein and separate the serum after clotting which is time-consuming and prone to contamination.

When the implant is to be used as a drug delivering device, a desired medicament 3 is placed in the reservoir compartment. To facilitate placement, the drug can be first compressed under high pressure into a pellet disc and pieces there from are inserted into the reservoir compartment. The reservoir compartment with the interconnected open-cell foam rings will restrain the solid drug pieces from entering the delivery compartment of the device, but not the dissolved drug. Just before use, the top polymer membrane covering the delivery compartment is pierced once with a needle to create an orifice 4. Since the membrane is elastic, the needle puncture is resealed which prevents leakage. Upon implantation subcutaneously, the serous fluid soon seeps into the empty device interior 1 under hydrostatic pressure through the puncture orifice, and dissolves some of the solid drug pieces in the reservoir compartment 3. If a dose of the drug is required, the interconnected flexible delivery compartment portion 5 of the implant is compressed sidewise externally over the skin fold by finger pressure. The sidewise compression reduces the internal volume of the delivery compartment, and thus sufficient pressure is created to expel the drug solution through the orifice at the center of the top membrane. Since the amount of the drug dissolved is determined by its solubility, the required dose to be dispensed ca be controlled by the delivery volume. While the expelled drug solution is absorbed and takes its effect over a period of several hours, the subcutaneous serous fluid gradually seeps into the just emptied device interior again through the resealable orifice to be ready for the delivery of the next dose. When the drug is depleted, a suspension of the same or another drug can be injected percutaneously into the reservoir compartment 2 sidewise through the rubbery rim 5 without the need to explant the emptied device and implantation of a new one.

The use of silicone material for the construction of the implantable device of the instant invention is because of the well-known biocompatibility of this synthetic polymer. Further, in fabricating the prototype device for testing to establish the validity and reliability of its operating principles, the silicone materials are easy to work with. From time to time new materials of comparable physicochemical properties and biocompatibility become available and can be used in combination with or even substitute the silicones in the fabrication of the implantable device of the instant invention. Notably, these alternative materials can be found in a category referred to as the segmented polyester-urethane and segmented polyether-urethane elastomers which can be formulated to produce resilient foams, elastic rubbers, rigid plastics as well as strong flexible membranes. As well, suitable natural materials can also be used to exchange for parts of the implantable device of the present invention. Therefore, in a combination of materials, the silicone foam rings can be replaced with rings cut from medical-grade natural sea sponge. The membrane layers sealing the top and bottom surface of the porous foam rings can be cast from polyisoprene, polysulfone, the Lycra (trade mark of E. I. DuPont and Co., Wilmington, Del.) polyurethane or natural elastomers, such as purified rubber. The adhesive and sealent required to attach the covering membrane layers to the foam rings and enclose the space around the external edges of the foam rings can remain to be the room temperature setting Silastic Type A resin (Dow Corning Corp., Midland, Mich.) or a suitable synethetic rubber formulation. As well, the reservoir compartment enclosure which does not need to be flexible may be fabricated from stainless steel, titanium, gold, other inert metals, alloys, ceramics, glass, synthetic polymers, such as polyalkylmethacrylate, polystyrene, epoxy composites, polyolefins, polyamides, polysulfones, or combinations of these materials known to be biocompatible. For refill or withdrawal from a rigid reservoir compartment, a resealable septum made of elastic material can be installed to facilitate the entry of a hypodermic needle. If required, a layer of membrane with a resealable orifice for serous fluid inflow may be positioned over and attached to a small opening on top of the rigid compartment shell. A flexible delivery compartment, if required, may also be attached and interconnected alongside with such reservoir compartment just mentioned.

In an embodiment of the present invention to prepare the test animal for collection of specific antibodies, 0.5 mg bovine serum albumin in Freund's complete adjuvant is injected intraperitoneally into a male rat weighing 180 g. After 3 days, a device is implanted which has been made with 2 foam rings 6 and 7 of O.D. 1 cm and I.D. 8 mm attached to each other tangentially at the circumference before being sealed around 9 and in between the membrane layers 8, with the top membrane having an orifice 4 pierced thereon. After another 2 days, about 0.3 mL of serous fluid can be withdrawn from the implant by a syringe with a 30-gauge needle inserted perpendicularly sidewise through the silicone rubber side rim 9. As the needle being so small, the test animal will show no objection or sign of discomfort. The serous fluid just obtained is transferred into a 3-mm diameter test tube, and an equal volume of a 0.2% bovine serum albumin solution is carefully layered on top of the collected serous fluid. After 1 hr, a milky ring developed at the interface which, indicates the formation of the specific antigen-antibody complex. Further amount of the immune fluid can be withdrawn daily, if required, and the presence of the specific antibodies evaluated by the milky ring test aforementioned. If a more intense immune response with a higher antibody concentration in the serous fluid is required, a booster antigen dose can be administered to the already sensitized animal. Again, after a few days, an anti-serum with more intense antigen-antibody complex formation can be harvested as aforementioned from the implanted device.

In the delivery of a bioactive macromolecule, such as insulin for control of hyperglycemia, somatotropin or somatocrinin or the like for promoting growth, etc., it is particularly important to have an implantable device which will eliminate the need for daily injections. In addition, bioactive polypeptides are often not very soluble in buffer solutions formulated for injection. Even once dissolved, they are not stable and often precipitate therefrom. However in the present invention, it is found that insulin and somatotropin are relatively stable and moderately soluble in serum. The amount of the serum which dissolves these bioactive macromolecules is set by the internal volume of the device which consists of the delivery and reservoir compartments, and thus the amount of the drug dissolved is determined by its solubility. If a larger dosage is required, the implant may be fabricated with larger foam rings to accommodate the serous fluid volume that will dissolve a larger amount of the solid drug until saturation.

In another embodiment of the instant invention a device fabricated as aforementioned with the foam ring size of O.D. 5 mm and I.D. 4 mm to serve as the reservoir compartment 2 which is attached to a delivery compartment 1 made of another foam ring of O.D. 8 mm and I.D. 5 mm. A 6-mg piece of solid insulin 3 and 2 mg tetracycline as an antibiotic agent are included in the reservoir compartment 2. After sealing the device, the top membrane of the delivery compartment is pierced, before the device is implanted under the abdominal skin of a diabetic Wistar rat. On the next day, sufficient serous fluid seeps into the device interior to dissolve some insulin from the solid piece. Upon external sidewise compression of the flexible delivery compartment over the skin fold to expel the drug solution, the blood glucose level of the diabetic animal decreased from >22 mM/L to 3.8 mM/L which is quite close to the normal range. After 21 daily compressions, the insulin supply is depleted. Another 6 mg insulin was suspended in distilled water containing 5% tetracycline and injected sidewise into the reservoir compartment 2 through the thick silicone rubber rim 5. The replenishment lasted 19 daily compressions with similar reduction of hyperglycemia.

In still another embodiment of the present invention, the device has a porous foam ring 6 with O.D. of 1 cm and I.D. of 8 mm as the delivery compartment 1, and another 6-mm O.D. by 4-mm I.D. foam ring 7 for reservoir compartment 2 which contains 12 mg of compressed bovine somatotropin 3 and 2 mg tetracycline. After sealing the rim 9 and the membranes 8 with the room temperature setting silicone rubber as aforedescribed, the top membrane of the flexible delivery compartment is punctured once with an 18-gauge needle which creates a resealable orifice 4 that will allow sufficient inflow of the serous fluid into the device in 1 day. The device is then implanted into a prepubertal female hypophysectomized Wistar rat which will not otherwise gain in body weight due to lack of its own growth hormone caused by surgical damage to the pituitary gland. After few days for the fragile animal to fully recovery from the implantation surgery, the flexible delivery compartment is compressed externally as before to discharge the somatotropin-containing serous fluid in the device. Next day, weighing showed that the otherwise stunted animal has now grown from 153 g to 158.7 g in 24-hr. Several compressions to deliver the growth hormone in the device result in an average growth of about 4.4 g per compression. After the device is depleted, a percutaneous refill of the implant with more bovine growth hormone, followed by daily compressions results in further growth stimulation.

The invention can be further illustrated by the following examples which are not intended to limit the scope of the present invention.

EXAMPLE 1

A candle wax slab (0.5 cm thick) is cast in a small plastic Petri dish (5 cm in diameter). A size 4 (1 cm in the wax slab with their circumferences tangentially in good contact. About 3 g of a silicone foam resin (Catalog No. Q7—9100, Dow Corning Corporation, Midland, Mich.) is transferred into a plastic weighing boat, followed by the addition of 2 drops of the polymerizing catalyst supplied with the resin kit package. The foaming mixture was stirred vigorously for 15 sec, and then poured into the aforementioned wax mould. After 5 min, the liquid solidifies into an elastic porous foam and can be lifted readily from the mould. The centers of the flat bicircular piece are cut by a size 3 (8 mm in diameter) cork borer to produce 2 foam rings fused at the external circumference to appear as a figure eight.

The required top and bottom membrane is cast by dissolving 11 g of a silicone paste (Room-Temperature-Curing Silicone Adhesive Type A, Dow Corning, Midland, Mich.) in 40 mL chloroform and pouring the solution into a flat Teflon-coated pan (20 cm in diameter). After the evaporation of the solvent in 5 hr at room temperature, the pan and its content are left in a 50° C. oven overnight. The next morning, a uniform membrane (about 0.5 mm thick) can be readily peeled off the pan surface and cut to size as required.

To assemble the implant, the top and bottom rim surfaces of the foam ring piece are evenly coated with the silicone adhesive paste aforementioned, and layered between 2 sheets of the silicone membrane (4 cm by 2 cm). Since a good contact is essential to ensure a complete seal between the foam surface and the membrane, the assembly is placed between 2 Plexiglas plates and held evenly in place by several small C-clamps around the plate edges. When the silicone adhesive paste solidifies in 2 hr, the C-clamps and the Plexiglas plates are removed. Generous amount of the silicone adhesive paste is then applied directly from the squeeze tube to the space between the top and bottom membrane extensions to seal around the side of the foam rings to a thickness of 5 mm. After 24 hr at room temperature, the thick silicone paste layer solidifies to become an elastic rubber which is then trimmed by a safety razor blade to a uniform thickness of 2 mm all around the bicircular foam rings. Before implantation, the reservoir device is immersed for several hours in a 10% Betadine solution for sterilization of the exterior surface. To eliminate microbial growth inside the device, few drops of a 5% tetracycline solution is injected through the thick silicone rubber rim. Finally, an 18-gauge hypodermic needle is used to puncture the top membrane at the center of 1 or both of the 2 foam rings to serve as orifice for serous fluid inflow.

About 3 days before the implantation of the reservoir device, a male Wistar rat (body weight: about 180 g) is given an intraperitoneal injection of 0.5 mg bovine serum albumin dissolved in 0.5 mL of normal saline and emulsified with an equal volume of Freund's Complete Adjuvant. At the time of implanting the reservoir device, the lymphoid cells of the immunized Wistar rat will usually begin to respond by releasing, into the circulation and serous fluid present in subcutaneous tissue layers, specific antibodies against the injected bovine serum albumin.

Sufficient amount of the antibody containing serous fluid will seep into the interior of the reservoir device in 24 hr after implantation, and on the day thereafter, about 0.3 mL of serous fluid can be withdrawn percutaneously from the unsedated animal by a syringe with a 30-gauge needle inserting perpendicularly sidewise into the reservoir through the silicone rubber rim. An amount of 0.1 mL of the immune serum just obtained is added to the bottom of a small test tube (3 mm in diameter), and an equal volume of a 0.2% bovine serum albumin solution is carefully layered thereon. Without disturbing the test tube content in anyway, the specific antigen-antibody interaction at the interface of the 2 liquids lead to the formation of a precipitate in a few hours which appears as a milky ring across the mid section of the liquid column. Daily withdrawals provide 0.3 to 0.5 mL samples each day, and the presence of the specific anti-bovine serum albumin antibodies can be detected by the ring test aforementioned for 2 to 3 weeks. At the end of the third week after implantation of the device, a booster antigen dose consisting of 0.2 mg bovine serum albumin in normal saline is injected intraperitoneally. Within the next 2 days, serous fluid withdrawn percutaneously from the implanted reservoir device is found to give a very dense milky precipitate in the ring test which persist even after several-fold dilution of the fluid sample indicating an intense secondary response to the booster antigen dose. The antibody containing fluid can be sampled daily for another 3 to 4 weeks before a new booster dose is required.

EXAMPLE 2

A wax mould with 2 wells fused tangentially at the circumference is cast essentially as described in Example 1. The first well has a diameter of 8 mm, and the smaller second well interconnected thereto has a diameter of 5 mm. The wax mould is then used to make a silicone foam slab in the form of 2 fused circular disks as already described in the preceding Example. The center of the large foam disk is cut to form a ring with I.D. of 5 mm (henceforth referred to as Ring A) using a size 2 cork borer, and the small disk attached next to it at the side is bored to form a ring of 4 mm I.D. (henceforth referred to as Ring B). Before sealing the porous foam rings between the silicone membrane layers and around the side with the silicone adhesive paste as described in detail given under Example 1, a rigid polyethylene cylinder (O.D. 4 mm, I.D. 2 mm, height: 4 mm) with holes pierced evenly spaced around mid height by an 18-gauge hypodermic needle, and about 6 mg insulin (activity: 24 U/mg) mixed with 2 mg tetracycline are placed inside the space of Ring B. The polyethylene cylinder is used to impart rigidity to Ring B, and the holes around the cylinder wall is to allow the passage of a 22-gauge needle used later for refilling with an insulin suspension. With a rigid Ring B, serous fluid therein will not be squeezed out when the delivery compartment is compressed to discharge the intended volume in Ring A. The device thus fabricated is immersed several hours in a 10% Betadine solution for sterilization of its external surface, thereafter the center of the top membrane covering Ring A is pierced once with an 18-gauge needle to create a resealable orifice for serous fluid inflow and later, the orifice will be used as an exit for the discharge of dissolved medicament when the delivery compartment is compressed.

A drop of blood is obtained from a male Wistar rat (body weight: about 250 g) by needle puncture of the tip of its tail and smeared evenly over the white reaction zone at the end of a blood glucose testing reagent strip (Dextrostix made by Miles Laboratories Ltd., Etobicoke, Ontario, Canada). After 1 min, the blood smear is washed off, and the now light blue reaction zone at the end of the strip is inserted into the reflectance photometer (Glucometer by Miles Laboratories Ltd.) which shows the normal blood glucose level of 5.5 mM glucose/L blood. This Wistar rat is then injected with streptozotocin (75 mg/kg body weight) by the tail vein which causes diabetes mellitus when tested the next day with its blood glucose at >22 mM/L. Without daily injection of insulin, hyperglycemia persists and the animal loses weight progressively until death occurs after 36 days. In another normal Wistar rat of similar body weight and made diabetic by streptozotocin injection, the insulin containing device fabricated and Betadine solution sterilized as just described is implanted subcutaneously under its closely shaved abdominal skin through an 1.5 cm incision, and the wound is closed with 2 small Michel clips. Overnight, sufficient serous fluid will seep through the orifice on the top membrane over Ring A to dissolve some of the insulin solid in Ring B until saturation. On the next morning, the flexible Ring A portion of the implant is held over the skin fold between the thumb and index fingers and compressed sidewise to expel the insulin containing fluid therein. When tested after 0.5 hr, the hyperglycemic blood glucose level of the diabetic rat decreased from >22 mM/L to 4.1 mM/L. Successive hourly tests show that the blood glucose level remains around 3.7 ±1.1 mM/L for 6 hr after the external compression of the implant for insulin delivery. Thereafter, the blood glucose level begins to elevate and when tested the next morning hyperglycemia at >22 mM glucose/L blood has recurred. When the subcutaneous implant is compressed externally again as the day before, the blood glucose of the hyperglycemic animal decreases from >22 to 3.5 ±1 mM/L for at least 6 hr and returns to become hyperglycemic overnight as before. The drug delivery implant undergoes 21 additional daily compressions, before further compressions show no reduction of hyperglycemia.

To refill the implant in the unsedated animal, an amount of 10 mg insulin is suspended in 0.5 mL normal saline, and 0.3 mL which contains 6 mg insulin is injected percutaneously with a 22-gauge hypodermic needle piercing the thick silicone sidewall and passing through a hole on the side of the protective polyethylene cylinder to enter into the interior of the Ring B compartment of the implant device. On the next day, external sidewise compression of the refilled implant reduced the blood glucose of the diabetic rat from >22 mM/L to 16.7 mM/L. On the following day and for 18 more daily compressions, its blood glucose level is consistently reduced each time from >22 to 3.5 ± 0.9 mM/L for at least 6 hr before hyperglycemia recurs. Another similar refill with 10 mg insulin suspension provides 29 daily compressions which result consistently in the daily reduction of hyperglycemia from >22 to 4.1 ± 1.3 mM/L as before. As well, this study shows that the insulin remains potent as a blood glucose lowering agent after prolonged contact with serous fluid at body temperature.

In the 73-day study, the diabetic test animal, maintained on daily doses of insulin delivered by external compression of the flexible Ring A compartment, remained healthy and grew from 285 g to 369 g.

EXAMPLE 3

Another device is fabricated essentially as described in Example 1 and Example 2, but consists of 3 different size silicone porous foam rings fused in a row at their circumferences. The external measurement of the device from one end of the silicone rubber edge to the other is 2.5 cm. Its external width in the center is 1.4 cm and the thickness is 6 mm. The first ring has O.D. 4 mm and I.D. 2 mm. The second ring in the middle has O.D. 9 mm and I.D. 6 mm. In addition, the second ring encloses a rigid polyethylene or Nylon cylinder (O.D. 6 mm and I.D. 4 mm) with holes around the cylinder wall pierced by an 18-gauge hypodermic needle as described in Example 2 to impart rigidity. The third ring, which is on the opposite side of the smaller first ring, has 6 mm as the O.D. and 4 mm as the I.D. In this 3 compartment device, the orifice made by puncture with an 18-gauge needle is at the center of the top membrane of the third ring.

The total internal volume of this 3-compartment device is determined by injecting distilled water into the second ring at the silicone rubber sidewall with the needle going through 1 of the holes on the rigid polyethylene cylinder to reach the inside of the ring space. Since the density of water is about unity, the weight difference before and after filling the 3-compartment device indicates that the total internal volume is 543 ± 15 uL. When the first ring is compressed sidewise, 29.3 ± 6 uL of the water is discharged through the orifice on the third ring compartment. Without refilling, a subsequent compression of the third ring expels 93.4 ± 10 uL. All the aforementioned in vitro tests are done, at least, in triplicate. As well, these tests demonstrate that by varying the size of the ring or the number of rings in the device, different delivery volumes can be obtained.

EXAMPLE 4

An implantable device fabricated essentially according to the details described in Example 1 and Example 2. The O.D. of the first silicone foam ring is 1 cm, and its I.D. is 8 mm. The smaller second silicone foam ring moulded next to it in a row to appear like a figure "8" in configuration (FIG. 1) has 8 mm and 6 mm for O.D. and I.D., respectively. The perforated rigid Nylon cylinder with O.D. 6 mm and I.D. 4 mm is placed inside the smaller second ring which will be used as the reservoir compartment. Flakes of bovine somatotropin in the amount of 12 mg (activity: 1 U/mg) and 2 mg tetracycline are inserted into the space inside the protective Nylon ring, before the foam rings are sealed in between the membrane layers and all around with the silicone paste which soon sets to become a rubber. After the excess membrane layers are cut, and the silicone rubber sidewall surrounding the foam rings is trimmed to a thickness of 2 mm, the fully assembled 2-compartment device is immersed in Betadine for sterilization. An 18-gauge needle is used to create a resealable orifice at the center of the top membrane over the larger first ring which is the delivery compartment, just before implantation under the cleanly shaved abdominal skin of an anesthetized female prepubertal Wistar rat (body weight: 153 g). This test animal has been previously hypophysectomized to destroy the growth hormone secreting capacity of its pituitary gland, and therefore it is no longer capable of gaining body weight without exogenous replenishment of the growth promoting polypeptide hormone. In a few days, when the skin incision next to the implant site is well healed, the flexible first ring of the device in the unsedated animal is compressed sidewise between fingers over the skin fold. The frequency of the external compression and the body weight gain of the hypophysectomized Wistar rat are shown in the following table:

TABLE 1

Body Weight Increase of Hypophysectomized Wistar Rat Following Delivery of Bovine Somatotropin by External Compression of the Implant

| Days post Implantation | Sequence of Compression | Next Day Body Weight (g)* | Daily Body Weight Gain (g) |
|---|---|---|---|
| 0 | 0 | 153.0 | 0 |
| 1 | none | 155.4 | 2.4 |
| 2 | none | 151.6 | −3.8 |
| 3 | none | 152.9 | 1.3 |
| 4 | 1st | 152.1 | −0.8 |
| 5 | 2nd | 158.7 | 6.6 |
| 6 | 3rd | 162.9 | 4.2 |
| 7 | 4th | 167.0 | 4.1 |
| 8 | 5th | 175.3 | 8.3 |
| 9 | none | 180.4 | 5.1 |
| 10 | none | 180.0 | −0.4 |
| 11 | none | 180.6 | 0.6 |
| 12 | 6th | 179.3 | −1.3 |
| 13 | 7th | 182.5 | 3.2 |
| 14 | 8th | 187.9 | 5.4 |
| 15 | 9th | 190.3 | 2.4 |
| 16 | 10th | 196.7 | 6.4 |
| 17 | 11th | 196.1 | −0.6 |
| 18 | 12th | 196.5 | 0.4 |
| 19 | 13th | 196.7 | 0.2 |
| 20 | 14th | 197.1 | 0.4 |

*Always taken at 3 p.m. the next afternoon.

In the 20-day study, the otherwise-stunted Wistar rat gains 44.1 g in body weight as a result of the 10 compressions. When further external compression beyond number 11 (second column in Table 1) on the 17th day and onwards show minimal change in body weight, 10 mg bovine somatotropin and 2 mg tetracycline are suspended in 0.5 mL normal saline, and 0.3 mL which contains 6 mg hormone is injected into the second ring percutaneously by a size 22-gauge hypodermic needle. The external compression is resumed for 8 consecutive days, but no further body weight gain is observed beyond the 5th day. After the refill of the implanted device, the body weight of the hypophysectomized rat shows increase of 14.7 g in the 5 days. Therefore, the 2 runs show that about 1 mg of the growth hormone is delivered by each compression of the implant resulting in 3.7 ±0.8 g of body weight increase on the following day. This study again shows that the polypeptide hormone, like insulin described in Example 2, remains active after many days in the serous fluid.

It will be understood that the above examples are illustrative only, and the invention is not limited thereto.

I claim:

1. A self contained implantable device having a porous central body and an external self-sealing skin which is easily penetrable by a needle, said skin having a resealable orifice, whereby said central body comprises a reservoir compartment for serous fluid and said orifice permits serous fluid entry after implantation.

2. A self contained implantable device as claimed in claim 1 wherein the central body comprises a plurality of interconnected porous sections.

3. A self contained implantable device as claimed in claim 2 wherein said central body comprises foam.

4. A self contained implantable device as claimed in claim 3 in which said central body is formed by a pair of foam rings having a figure 8 cross section.

5. A self contained implantable device as claimed in claim 3 wherein a porous section contains a bioactive substance.

6. A self contained implantable device as claimed in claim 2 wherein a porous section contains a bioactive substance.

7. A self contained implantable device as claimed in claim 6 wherein said bioactive substance if a solid.

8. A self contained implantable device as claimed in claim 6 wherein said bioactive substance is carried within a penetrable relatively rigid structure disposed within said porous section.

9. A self contained implantable device as claimed in claim 6 wherein the bioactive substance is a polypeptide hormone.

10. A self contained implantable device as claimed in claim 6 wherein the polypeptide hormone is insulin, somatotropin, somatomedin, or mixture thereof.

11. A self contained implantable device as claimed in claim 6 wherein the bioactive substance is steroid hormone.

* * * * *